(12) United States Patent
Lee et al.

(10) Patent No.: US 11,524,038 B2
(45) Date of Patent: *Dec. 13, 2022

(54) METHODS FOR TREATING SARCOPENIA AND MAINTAINING OR INCREASING MUSCLE MASS AND MUSCLE STRENGTH IN ELDER SUBJECTS

(71) Applicant: SYNBIO TECH INC., Kaohsiung (TW)

(72) Inventors: Chia-Chia Lee, Kaohsiung (TW); Han-Yin Hsu, Kaohsiung (TW); Chi-Chang Huang, Taoyuan (TW); Yi-Ju Hsu, Taoyuan (TW); Mon-Chien Lee, Taoyuan (TW)

(73) Assignee: SYNBIO TECH INC., Kaohsiung (TW)

( * ) Notice: Subject to any disclaimer, the term of this patent is extended or adjusted under 35 U.S.C. 154(b) by 0 days.

This patent is subject to a terminal disclaimer.

(21) Appl. No.: 16/652,740

(22) PCT Filed: Jan. 16, 2020

(86) PCT No.: PCT/IB2020/050325
§ 371 (c)(1),
(2) Date: Apr. 1, 2020

(87) PCT Pub. No.: WO2020/260958
PCT Pub. Date: Dec. 30, 2020

(65) Prior Publication Data
US 2021/0008131 A1    Jan. 14, 2021

(30) Foreign Application Priority Data

Jun. 25, 2019   (TW) .................................. 108122113

(51) Int. Cl.
| | |
|---|---|
| A61K 35/747 | (2015.01) |
| A61K 35/00 | (2006.01) |
| A61P 21/00 | (2006.01) |
| A61K 9/00 | (2006.01) |

(52) U.S. Cl.
CPC .......... *A61K 35/747* (2013.01); *A61K 9/0056* (2013.01); *A61P 21/00* (2018.01); *A23Y 2220/67* (2013.01); *A61K 2035/115* (2013.01)

(58) Field of Classification Search
None
See application file for complete search history.

(56) References Cited

U.S. PATENT DOCUMENTS

| | | |
|---|---|---|
| 10,188,685 B2 | 1/2019 | Chen et al. |
| 2018/0055893 A1* | 3/2018 | Chen ...................... A61K 35/65 |

OTHER PUBLICATIONS

Huang et al. Nutrients 11: 2836: 1 of 15-15 of 15, Nov. 19, 2019.*
Huang et al. Chinese J. Physiol. 61: 163-170, Jun. 2018.*

* cited by examiner

*Primary Examiner* — S. Devi
(74) *Attorney, Agent, or Firm* — Nixon & Vanderhye, P.C.

(57) ABSTRACT

Disclosed herein is a composition including *Lactobacillus plantarum* TWK10 deposited at the China General Microbiological Culture Collection Center (CGMCC) under accession number CGMCC 13008 for use in treating sarcopenia and for use in maintaining and/or increasing muscle mass and/or strength in an elderly subject.

7 Claims, 2 Drawing Sheets

METHODS FOR TREATING SARCOPENIA AND MAINTAINING OR INCREASING MUSCLE MASS AND MUSCLE STRENGTH IN ELDER SUBJECTS

This application is the U.S. national phase of International Application No. PCT/IB2020/050325 filed Jan. 16, 2020 which designated the U.S. and claims priority to TW Patent Application No. 108122113 filed Jun. 25, 2019, the entire contents of each of which are hereby incorporated by reference.

FIELD

The disclosure relates to use of a composition including *Lactobacillus plantarum* for treating sarcopenia and for maintaining or increasing muscle mass and muscle strength in elder subjects.

BACKGROUND

Sarcopenia, which is the degenerative loss of skeletal muscle mass, quality, and strength associated with aging and immobility, commonly affects elder subjects over the age of about 60. The rate of muscle loss is dependent on exercise level, co-morbidities, nutrition and other factors. A decline in muscle mass and strength in elders often manifests reduced physical functional capacity, leading to lower quality of life and an increased risk of adverse health events (e.g., falls and fractures subsequent thereto).

Although the mechanisms of muscle changes of sarcopenia have yet to be well clarified, exercise (such as resistance training) remains the intervention of choice for sarcopenia. In addition, ensuring adequate nutrition (e.g., proteins, calcium and vitamin D, etc.) in elder subjects is of interest in preventing the progression of sarcopenia.

U.S. Patent Publication No. 10188685 B2 discloses that *Lactobacillus plantarum* TWK10 (also named as *Lactobacillus plantarum* LP10) with the deposition number CGMCC 13008 is capable of improving exercise performance and reducing muscle fatigue. In this patent, six-week-old mice (i.e., adolescent mice) were used in the experiments to demonstrate that pretreatment with *Lactobacillus plantarum* TWK10 can increase the exhaustive swimming time of the mice and improve the forelimb grip strength of the mice. However, it is noted that the physical and physiological conditions of subjects at different life periods (such as nursing, adolescent, adult, and aged stages, etc.) are diverse, which might affect their drug response to the same substance. That is, age may be an unpredictable factor causing a variable response to drugs, and thus different treatment strategies may be needed for the subjects at different life periods.

SUMMARY

Therefore, in a first aspect, this disclosure provides a composition for use in treating sarcopenia, the composition including *Lactobacillus plantarum* TWK10 which is deposited at the China General Microbiological Culture Collection Center (CGMCC) under accession number CGMCC 13008.

According to a second aspect, this disclosure provides use of *Lactobacillus plantarum* TWK10 for the manufacture of a composition for treating sarcopenia.

According to a third aspect, this disclosure provides a method for treating sarcopenia, which includes administering to a subject in need thereof the aforesaid composition in the first or second aspect.

In addition, in a fourth aspect, this disclosure provides a composition for use in maintaining and/or increasing muscle mass and/or strength in an elderly subject, the composition including *Lactobacillus plantarum* TWK10.

According to a fifth aspect, this disclosure provides use of *Lactobacillus plantarum* TWK10 for the manufacture of a composition for maintaining and/or increasing muscle mass and/or strength in an elderly subject.

According to a sixth aspect, this disclosure provides a method for maintaining and/or increasing muscle mass and/or strength in an elderly subject, which includes administering to the elderly subject the aforesaid composition in the fourth or fifth aspect.

BRIEF DESCRIPTION OF THE DRAWINGS

Other features and advantages of the disclosure will become apparent in the following detailed description of the embodiments with reference to the accompanying drawings, of which.

DETAILED DESCRIPTION

Figure 1:
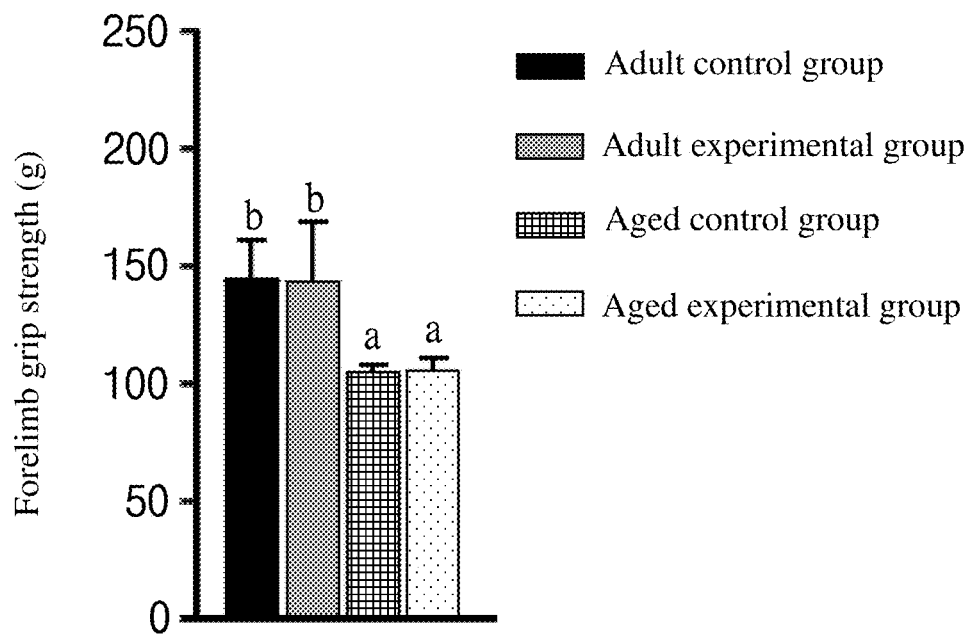
FIG. 1 shows the forelimb grip strength of the mice in the adult and aged control groups before administration, in which the symbol "***" represents $p<0.001$ when compared with the adult control group.

For the purpose of this specification, it will be clearly understood that the word "comprising" means "including but not limited to", and that the word "comprises" has a corresponding meaning.

Unless defined otherwise, all technical and scientific terms used herein have the meaning commonly understood by a person skilled in the art to which the present disclosure belongs. One skilled in the art will recognize many methods and materials similar or equivalent to those described herein, which could be used in the practice of the present disclosure. Indeed, the present disclosure is in no way limited to the methods and materials described. For clarity, the following definitions are used herein.

As used herein, the term "treating" or "treatment" refers to both therapeutic treatment and prophylactic or preventative measures, wherein the aim is to prevent, ameliorate, reduce or slow down (lessen) or improve a condition, disease or disorder.

As used herein, the term. "preventing", "prevention", "preventative" or "prophylactic" refers to keeping from occurring, or to hinder, defend from, or protect from the occurrence of a condition, disease, disorder, or phenotype, including an abnormality or symptom. A subject in need of prevention may be prone to develop the condition.

As used herein, the term "ameliorate" or "amelioration" refers to a decrease, reduction or elimination of a condition, disease, disorder, or phenotype, including an abnormality or symptom. A subject in need of treatment may already have the condition, or may be prone to have the condition or may be in whom the condition is to be prevented.

As used herein, the term "maintain" refers to sustaining a condition at pre-treatment levels.

The present disclosure provides a composition for use in treating sarcopenia, including *Lactobacillus plantarum* TWK10 which is deposited at the China General Microbiological Culture Collection Center (CGMCC) under accession number CGMCC 13008. The present disclosure also provides a composition for use in maintaining and/or increasing muscle mass and/or strength in an elderly subject.

As used herein, the term "sarcopenia" refers to degenerative loss of skeletal muscle mass (e.g., decrease in muscle fiber or muscle atrophy) and/or degenerative loss of skeletal muscle function (e.g., low muscle strength or reduced physical performance). Sarcopenia typically occurs during aging, but it may be a symptom of other conditions, such as obesity, stroke, advanced cancer, chronic kidney and heart failure, AIDS, etc. In certain embodiments, the sarcopenia is age-related sarcopenia.

As used herein, the term "subject" refers to any animal of interest, such as humans, monkeys, cows, sheep, horses, pigs, goats, dogs, cats, mice and rats. In certain embodiments, the subject is a human. As used herein, an "elderly" subject is one who experiences age related changes in at least one of body mass index and muscle mass and/or strength (e.g., age related sarcopenia) or who is afflicted with a disease or disorder characterized by decreased muscle mass or strength. In some embodiments, the elderly subject is one who has experienced a loss of muscle mass from peak lifetime muscle mass and/or strength by at least 5%, at least 10%, at least 15%, at least 20%, at least 25%, at least 30%, at least 35%, at least 40%, at least 45%, at least 50%, at least 55%, or at least 60%. Because age related changes to at least one of body mass index and muscle mass and/or strength are known to correlate with increasing age, in some embodiments, an elderly subject is identified or defined simply on the basis of age. Thus, in some embodiments, an "elderly" subject is identified or defined simply by the fact that their age is at least 50 years old, at least 60 years old, at least 65 years old, at least 70 years old, at least 75 years old, at least 80 years old, at least 85 years old, at least 90 years old, at least 95 years old, or at least 100 years old, and without recourse to a measurement of at least one of body mass index and muscle mass and/or strength.

According to the present disclosure, *Lactobacillus plantarum* TWK10 may be concentrated or non-concentrated, a liquid, a paste, a semi-solid, or a solid (e.g. a pellet, a granule, or powder), and may be frozen, dried, or freeze-dried (for example, may be in freeze-dried form or spray/fluid bed dried form).

In an exemplary embodiment, *Lactobacillus plantarum* TWK10 is in freeze-dried powder form.

In addition, this disclosure is directed to use of *Lactobacillus plantarum* TWK10 for the manufacture of a composition for treating sarcopenia.

This disclosure is also directed to use of *Lactobacillus plantarum* TWK10 for the manufacture of a composition for maintaining and/or increasing muscle mass and/or strength in an elderly subject.

In certain embodiments, the composition according to this disclosure is prepared in the form of a pharmaceutical composition. The pharmaceutical composition of this disclosure may further include a pharmaceutically acceptable carrier, and may be made into a dosage form suitable for oral administration using technology well-known to those skilled in the art. Examples of the oral dosage form include, but are not limited to, a solution, a suspension, an emulsion, powder, a tablet, a pill, syrup, lozenge, troche, chewing gum, a capsule, slurry and the like.

Examples of the pharmaceutically acceptable carrier suitable for use in this disclosure may include, but are not limited to, solvents, buffers, emulsifiers, suspending agents, decomposers, disintegrating agents, dispersing agents, binding agents, excipients, stabilizing agents, chelating agents, diluents, gelling agents, preservatives, wetting agents, lubricants, absorption delaying agents, liposomes, and combinations thereof. The choice and amount of the aforesaid pharmaceutically acceptable carriers are within the expertise and the routine skills of those skilled in the art.

In certain embodiments, the composition according to this disclosure is prepared in the form of a food composition, such as a food additive, which can be added into an edible material to prepare a food product for human or animal consumption. Examples of the food product according to this disclosure may include, but are not limited to: fluid milk products, e.g., milk and concentrated milk; fermented milk, e.g., yogurt, sour milk and frozen yogurt; milk powder; ice cream; cream cheeses; dry cheeses; soybean milk; fermented soybean milk; vegetable-fruit juices; fruit juices; sports drinks; confectionery; jelly; candies; health foods; animal feeds; and dietary supplements.

The present disclosure also provides a method for treating sarcopenia, which includes administering to a subject in need thereof the aforesaid composition.

In addition, this disclosure provides a method for maintaining and/or increasing muscle mass and/or strength in an elderly subject, which includes administering to the elderly subject the aforesaid composition.

The dosage and the frequency of administration of the composition according to this disclosure may vary depending on the following factors: the severity of the disease/disorder to be treated and the weight, age, physical condition and response of the subject to be treated. Generally, the daily dosage of the composition according to this disclosure may be administered in a single dose or in several doses.

The present disclosure will be further described in the following examples. However, it should be understood that the following examples are solely intended for the purpose of illustration and should not be construed as limiting the present disclosure in practice.

EXAMPLES

Example 1. Evaluation for Effect of *Lactobacillus plantarum* TWK10 on Treating Sarcopenia Experimental Materials:
1. *Lactobacillus plantarum* TWK10

*Lactobacillus plantarum* TWK10 strain (also named as *Lactobacillus plantarum* LP10) has been deposited at the China General Microbiological Culture Collection Center (CGMCC) (Institute of Microbiology, Chinese Academy of Sciences, No. 1 West Beichen Road, Chaoyang District, Beijing 100101, China) under accession number CGMCC 13008 since Sep. 13, 2016.

*Lactobacillus plantarum* TWK10 was inoculated in an amount of 3% (v/v) into MRS medium (BD Pharmingen™) serving as a seed medium, and then was cultured at 37° C. for 14 hours to 16 hours. The resultant seed culture was poured into the MRS medium as described above for large-scale expansion and was further cultured at 37° C. for 12 to 14 hours. After centrifugation at 1200 rpm and 4° C. for 20 minutes to 40 minutes, the resultant cell pellet was collected, followed by freeze-drying, so as to obtain freeze-dried powder of *Lactobacillus plantarum* TWK10 having a bacterial concentration of $3.0 \times 10^{11}$ CFU/g. Then, the freeze-dried powder was suspended in phosphate buffered saline (PBS) to obtain a suspension of *Lactobacillus plantarum* TWK10 for the following experiments.

2. Experimental Animals

Mature adult male ICR mice (at the age of 4 months and having an average weight of about 40 g) and aged male ICR mice (at the age of 19 to 22 months and having an average weight of about 40 g) were purchased from BioLASCO Taiwan Co., Ltd. The mice were kept in an animal room under the following laboratory conditions: a temperature of $24 \pm 2°$ C., a relative humidity of $65 \pm 5\%$, and a 12-hour light/12-hour dark cycle. Diet and water were provided ad libitum for all of the experimental animals. All animal experiments were conducted according to guidelines of Institutional Animal Care and Use Committee (IACUC) of the National Taiwan Sport University, Taiwan, and according to Guide for the Care and Use of Laboratory Animals of National Institutes of Health (NIH), U.S.A.

Experiential Procedure:

The mature adult mice were divided into an adult control group (n=8) an adult experimental group (n=9), and the aged mice were divided into an aged control group (n=9) and an aged experimental group (n=7). The mice in the adult and aged experimental groups were administered by oral gavage with the suspension of *Lactobacillus plantarum* TWK10 at a dose of $10^9$ CFU/kg, and the mice in the adult and aged control groups were administered by oral gavage with the same volume of PBS. Each mouse was subjected to administration once a day for a total experimental period of 12 weeks.

A. Determination of Forelimb Grip Strength

Before administration and after eight weeks of administration, each mouse was subjected to a forelimb grip strength test using a low-force testing system (Model-RX-5, Aikoh Engineering, Nagoya, Japan) and a force transducer attached to a metal bar (having a diameter of 2 mm and a length of 7.5 cm). To be specific, each mouse was held by its tail, and was dropped in a direction toward the metal bar to allow the mouse to grip the metal bar with its forelimbs. The mouse was then pulled by the tail in a direction away from the metal bar until the grip was broken, and the force thus generated was recorded by the force transducer. The above experiment was repeated 10 times, and a maximum value of these recorded forces was considered as the forelimb grip strength (in grams).

The experimental data are expressed as mean±standard deviation (SD) and were analyzed using unpaired t test so as to assess the difference between the groups. Statistical significance is indicated by $p<0.05$.

B. Measurement of Muscle Mass

After 12 weeks of administration, each mouse in the adult control group and in the adult and aged experimental groups was sacrificed, and gastrocnemius and soleus muscles in the back part of the lower legs were obtained and subjected to muscle mass determination.

C. Measurement of Cross-Section Area of Muscle Fiber

The gastrocnemius muscle of each mouse in the adult and aged experimental groups as obtained in the above section B was fixed in 10% formalin for 4 hours, and then was embedded in paraffin and sliced to obtain a tissue section having a thickness of 4 μm for morphological and pathological evaluations. The tissue section was stained with hematoxylin and eosin and was then examined and photographed using a light microscope equipped with a CCD camera (BX-51, Olympus, Tokyo, Japan) under 100× magnification. The cross-section area of the muscle fiber was determined using ImageJ software.

Results:

A. Forelimb Grip Strength

FIG. 1 shows the forelimb grip strength of the mice in the adult and aged control groups before administration. It can be seen from FIG. 1 that the forelimb grip strength of the aged control group was significantly lower than that of the adult control group, indicating that the mice in the aged control group had reduced muscle strength and might suffer from age-related sarcopenia.

Figure 2:
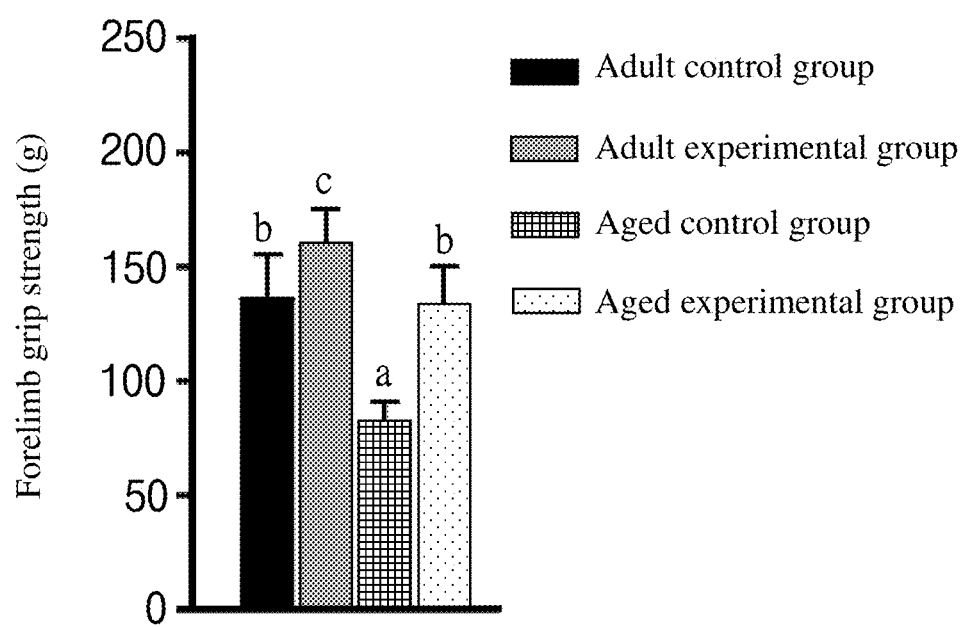
FIG. 2 shows the forelimb grip strength of the mice in each group after 8 weeks of administration, in which the mice in the adult and aged control groups were administrated with phosphate buffered saline (PBS), the mice in the adult and aged experimental groups were administrated with *Lactobacillus plantarum* TWK10, the symbol "" represents $p<00.01$ when compared with the adult control group, and the symbol "*" represents $p<0.001$ when compared with the aged control group.

FIG. 2 shows the forelimb grip strength of the mice in each group after 8 weeks of administration. It can be seen from FIG. 2 that the forelimb grip strength of the mice in the adult experimental group was increased as compared to the adult control group, and the forelimb grip strength of the mice in the aged experimental group was greatly improved as compared to the aged control group. The results indicate that *Lactobacillus plantarum* TWK10 is effective in maintaining, and even enhancing the muscle strength for the adult and aged mice, particularly for the aged mice. Therefore, *Lactobacillus plantarum* TWK10 is expected to improve the decreased muscle strength caused by aging.

B. Muscle Mass

The muscle mass of the mice after 12 weeks of administration is shown in Table 1. It can be seen that the mice of the aged control group had severely decreased muscle mass as compared to the adult control group. Taking the results shown in FIG. 1 and Table 1 together, it can be assumed that the aged mice were suffering from sarcopenia and had significant loss of muscle mass and strength. However, the muscle mass of the mice in the aged experimental group was increased, which indicates that *Lactobacillus plantarum* TWK10 is capable of improving loss of muscle mass caused by aging, and thus may be suitable for treating sarcopenia.

TABLE 1

|  | Muscle mass (mg) |
| --- | --- |
| Adult control group | 408 ± 22 |
| Aged control group | 263 ± 35 |
| Aged experimental group | 279 ± 70 |

C. Cross-Section Area of Muscle Fiber

Figure 3:
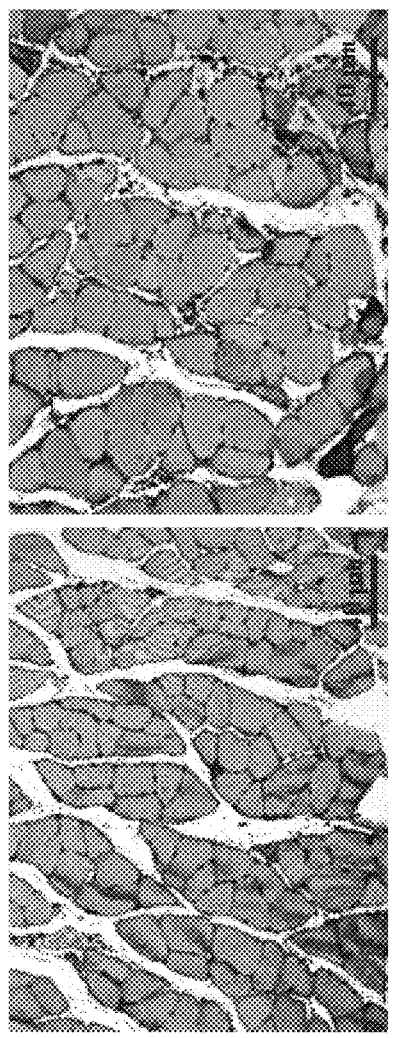
FIG. 3 shows the muscle mass of the mice in the aged control and experimental groups after 12 weeks of administration.

FIG. 3 shows the muscle mass of the mice in the aged control and experimental groups after 12 weeks of administration. It can be seen from FIG. 3 that as compared to the aged control group, the mice in the aged experimental group had muscle fibers with greater cross-section area, indicating that *Lactobacillus plantarum* TWK10 increases the size of the muscle fiber.

The above experimental results reveal that *Lactobacillus plantarum* TWK10 is able to effectively prevent and ameliorate the loss of muscle mass, to improve muscle strength and increase muscle fibers in the course of aging, thereby being capable of effectively treating sarcopenia.

All patents and literature references cited in the present specification as well as the references described therein, are hereby incorporated by reference in their entirety. In case of conflict, the present description, including definitions, will prevail.

In the description above, for the purposes of explanation, numerous specific details have been set forth in order to provide a thorough understanding of the embodiments. It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects, and that one or more features or specific details from one embodiment may be practiced together with one or more features or specific details from another embodiment, where appropriate, in the practice of the disclosure.

While the disclosure has been described in connection with what are considered the exemplary embodiments, it is understood that this disclosure is not limited to the disclosed embodiments but is intended to cover various arrangements included within the spirit and scope of the broadest interpretation so as to encompass all such modifications and equivalent arrangements.

What is claimed is:

1. A method of maintaining and/or increasing muscle mass and/or muscle strength in a human subject comprising administering to the human subject a single dose or several doses of a composition comprising *Lactobacillus plantarum* TWK10 which is deposited at the China General Microbiological Culture Collection Center (CGMCC) under accession number CGMCC 13008, wherein the human subject is at least 60 years old.

2. The method as claimed in claim 1, wherein the composition is a pharmaceutical composition that further includes a pharmaceutically acceptable carrier.

3. The method as claimed in claim 2, wherein the pharmaceutical composition is in an oral dosage form.

4. The method as claimed in claim 1, wherein the composition is a food composition.

5. The method as claimed in claim 1, wherein the human subject is at least 75 years old.

6. The method as claimed in claim 1, wherein the human subject is at least 85 years old.

7. The method as claimed in claim 1, wherein the human subject is at least 65 years old, at least 70 years old, or at least 80 years old.

* * * * *